(12) United States Patent
Matur et al.

(10) Patent No.: US 7,316,917 B2
(45) Date of Patent: Jan. 8, 2008

(54) PRODUCTION OF BICYCLIC-HETEROARYL-2-CARBOXYLIC ACIDS BY SELECTIVE ENZYMATIC HYDROLYSIS OF A MIXTURE OF POSITIONAL ESTERS

(75) Inventors: Ramesh Venkat Matur, Ridgewood, NJ (US); Mark Edward Ruppen, Garnerville, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 398 days.

(21) Appl. No.: 10/844,195

(22) Filed: May 12, 2004

(65) Prior Publication Data

US 2004/0229324 A1 Nov. 18, 2004

Related U.S. Application Data

(60) Provisional application No. 60/471,461, filed on May 16, 2003.

(51) Int. Cl.
C12P 17/18 (2006.01)
(52) U.S. Cl. .................................... 435/119
(58) Field of Classification Search .............. None
See application file for complete search history.

(56) References Cited

U.S. PATENT DOCUMENTS

2004/0242874 A1 12/2004 Winkley et al.

FOREIGN PATENT DOCUMENTS

| EP | 0 084892 A2 | 8/1983 |
|---|---|---|
| EP | 1 241 170 A2 | 9/2002 |
| WO | WO 94/10178 A1 | 5/1994 |
| WO | WO 03/093277 A1 | 11/2003 |

OTHER PUBLICATIONS

Berglund, P. and Hult, K.; Stereoselective Biocatalysis; pp. 633-657; 2000, from Applicants IDS.*
Inanaga, et al.; Bull. Chem. Soc. Jpn.; vol. 52; p. 1989; 1979.
Ranganathan, D., et al.; Tetrahedron Letters; vol. 24; No. 10; pp. 1067-1070; 1983.
Keller, J.W. and Hamilton, B.J.; Tetrahedron Letters; vol. 27; p. 1249; 1986.
Pirrung, M.C. and Krishnamurthy, N.; Org. Chem.; vol. 58; p. 954; 1993.
Morbidity and Mortality Weekly Report; vol. 42; No. 30; pp. 597-598; 1993.
Handwerger, S., et al.; Clin. Infect. Dis.; No. 16; pp. 750-755; 1993.
Berglund, P. and Hult, K.; Stereoselective Biocatalysis; pp. 633-657; 2000.
Zaks, A.; Curr. Opinion in Chem. Biol.; vol. 5; pp. 130-136; 2001.
Wang, C-H and Whitesides, G.M.; Tetrahedron Organic Chemistry Series, vol. 12; pp. 41-130, 1994.
J.N. Lee, et al.; Bull. Korean Chem. Soc.; vol. 21; No. 8; pp. 761-762; 2000.
Schmid, A., et al.; Nature; vol. 409; pp. 258-268; 2001.
B.G. Davis; V. Boyer; Nat. Prod. Rep.; vol. 18; pp. 618-640; 2001.
PCT/US2004/014833 International Search Report, Oct. 27, 2004.

* cited by examiner

*Primary Examiner*—Cscilia J. Tsang
*Assistant Examiner*—Thomas S. Heard
(74) *Attorney, Agent, or Firm*—Daniel B. Moran, Agent

(57) ABSTRACT

The invention relates to an enzymatic process for the production of an intermediate, bicyclic-heteroaryl-2-carboxylic acid 7, of the formula

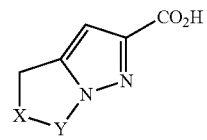

7 wherein X and Y are defined in the specification and which are useful in the preparation of beta-lactamase inhibitors, by selective enzymatic hydrolysis of a mixture of positional hydrolyzable esters of the formulae

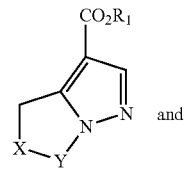

5 and

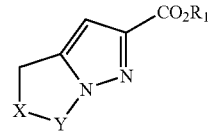

6 where X, Y, and $R_1$ are defined in the specification.

18 Claims, 3 Drawing Sheets

Scheme II

PRODUCTION OF BICYCLIC-HETEROARYL-2-CARBOXYLIC ACIDS BY SELECTIVE ENZYMATIC HYDROLYSIS OF A MIXTURE OF POSITIONAL ESTERS

"This application claims priority from now abandoned Provisional Application No. 60/471,461 filed May 16, 2003 the entire disclosure of which is hereby incorporated by reference".

FIELD OF THE INVENTION

The invention relates to an enzymatic process for the production of an intermediate, bicyclic-heteroaryl-2-carboxylic acid, useful in the preparation of beta-lactamase inhibitors, by selective enzymatic hydrolysis of a mixture of positional hydrolyzable esters.

BACKGROUND OF THE INVENTION

New improved antibiotics are continually in demand, for the treatment of diseases in man. Antibiotic resistant organisms are continually a problem, with Vancomycin the last defense, particularly in hospitals, vancomycin resistant strains are increasing among the hospital isolated pathogens. A recent survey found 7.9% of *Enterococci* in the United States hospitals are now vancomycin resistant. ("Nosocomial *Enterococci* Resistant to Vancomycin" Morbidity and Mortality Weekly Report 42(30):597-598(1993)). Further resistance of Vancomycin and other antibiotics to *Enterococcus faecium* is reported, (Handwergers. et al., Clin. Infect. Dis. 1993(16),750-755). Resistance organisms are also a problem for other important antibiotics which includes piperacillin. In an effort to overcome resistant organisms and to enhance the effectiveness of antibiotics by inhibiting the activity of a specific enzyme, beta-lactamase, which is produced by certain drug-resistant strains of bacteria, beta-lactamase inhibitors are combined with antibiotics or concurrently administered.

Clearly, antibiotic resistance is a growing public health problem and having new antibiotics available could provide additional options for physicians in treatment regimens. Further, the medical community recognizes that there is an ongoing need for additional antibiotics and concurrently that beta-lactamase inhibitors are useful for enhancing presently available antibiotics to which resistance has developed. The preparation of new beta-lactamase inhibitors requires processes that can efficiently produce intermediates necessary for the preparation of the final beta-lactamase products. As in the case of many synthetic procedures, mixtures of compounds are produced which require chromatographic separations for purification.

The present invention overcomes the problems of purification and separation of mixtures by presenting an alternate method for preparing a single carboxylic acid intermediate through a selective enzymatic hydrolysis of one ester isomer in a mixture of positional ester isomers. Use of hydrolases such as lipases, esterases or proteases for separation of chiral molecules by kinetic resolution is very well established in the literature, (Zaks, A,. Curr. Opinion in Chem Biol. 2001, 5, 130-136.; Wang, C -H and Whitesides G. M. In Enzymes in synthetic organic chemistry: Tetrahedron organic chemistry series vol. 12: pp. 41-130, Pergamon press; Berglund P, and Hult, K. Biocatalytic synthesis of enantiopure compounds using lipases, pp 633-657, In "Stereoselective biocatalysis", ed. Patel, R. N. Marcel Dekker Inc., 2000).

Preferential cleavage by enzymes of one of the ester groups present on the same molecule (also described as regiospecificity) is also known, (Keller, J. W, Hamilton, B. J., Tetrahedron Letts.1986, 27, 1249.; Pirrung M. C., and Krishnamurthy N., J. Org. Chem. 1993, 58, 954).

However, selective hydrolysis of positional ester isomers by enzymatic hydrolysis and separation of the desired resulting carboxylic acid intermediate compounds described in the present invention is not known.

BRIEF SUMMARY OF THE INVENTION

Figure 1:
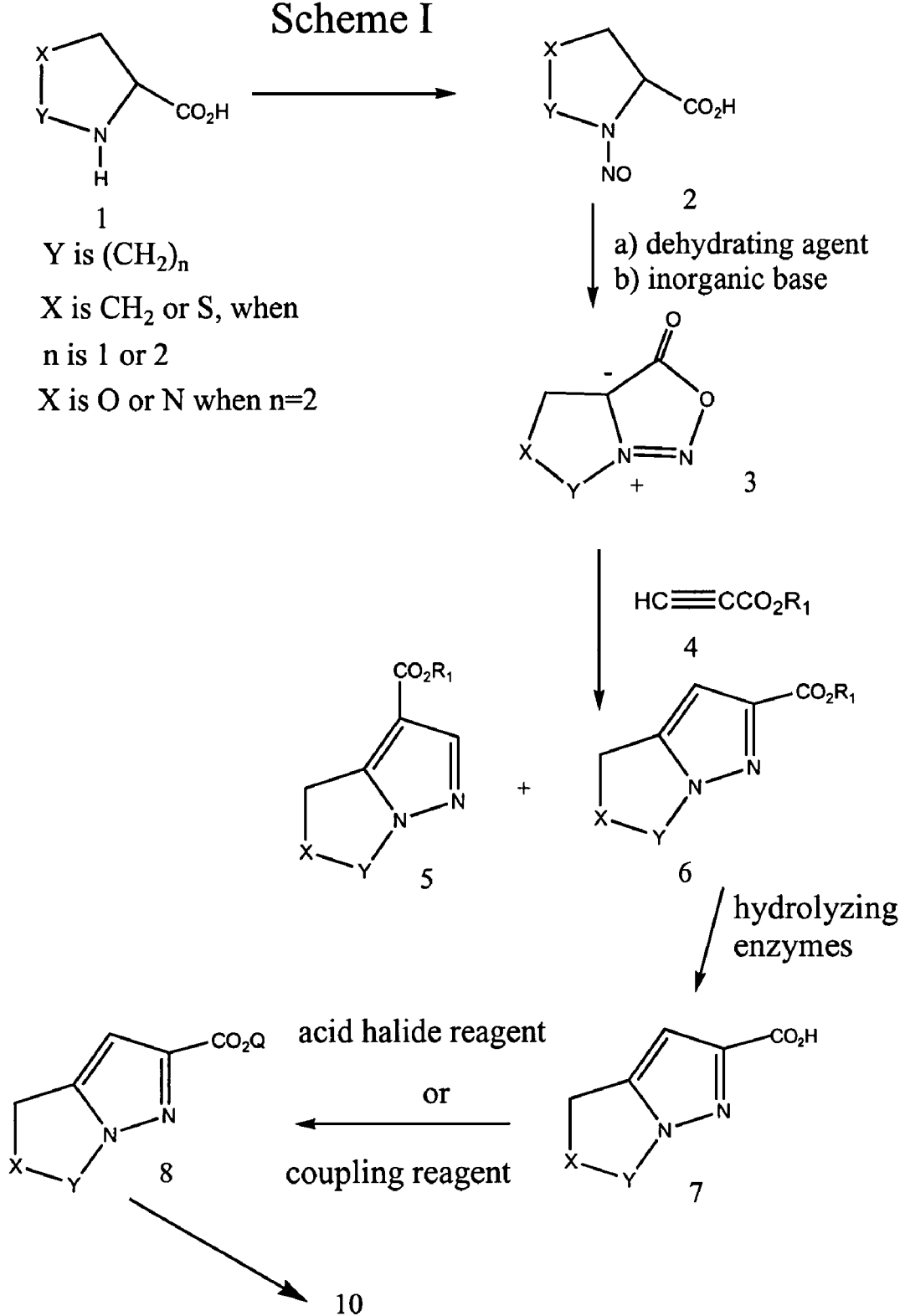
FIG. 1 Scheme I
FIG. 2 Scheme I Continued
FIG. 3 Scheme II

The invention relates to a process for the preparation of bicyclic-heteroaryl-2-carboxylic acid 7 of the formula

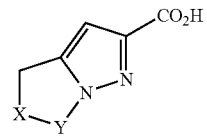

7 wherein Y is $(CH_2)_n$; n is 1 or 2; X is —NR, O, S or —$CH_2$—; R is alkyl of 1 to 6 carbon atoms, or arylalkyl($C_1$ to $C_6$); provided n is 2 when X is NR or O which comprises enzymatic hydrolysis of bicyclic-heteroaryl-2-carboxylic acid ester 6 wherein X, Y and R are defined as above or selectively in a mixture of bicyclic-heteroaryl-2-carboxylic acid ester 6 and bicyclic-heteroaryl-3-carboxylic acid ester 5 wherein X and Y are defined as above and $R_1$ is alkyl of 1 to 6 carbon atoms of the formulae:

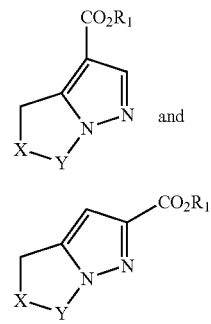

5 and

6 to produce a bicyclic-heteroaryl-2-carboxylic acid 7 of the formula

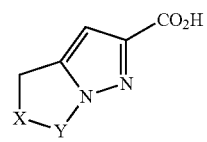

7 wherein X and Y are defined as above and isolating a bicyclic-heteroaryl-2-carboxylic acid 7.

Alkyl is straight or branched chain alkyl moieties of 1 to 6 carbon atoms.

Arylalkyl($C_1$ to $C_6$) means an alkyl moiety of 1 to 6 carbon atoms substituted with an aryl moiety wherein the aryl moiety is defined as an aromatic hydrocarbon moiety having 6 to 12 carbon atoms and selected from the group: phenyl, α-naphthyl, β-naphthyl, biphenyl, anthryl, tetrahydronaphthyl, fluorenyl, indanyl, biphenylenyl, and acenaphthenyl. Arylalkyl($C_1$ to $C_6$) moieties include benzyl, 1-phenylethyl, 2-phenylethyl, 3-phenylethyl, 2-phenylpropyl, 4-nitrobenzyl and the like.

Previously, intermediate bicyclic heteroaryl-2-carboxylic acids were prepared from a mixture of positional esters which required chromatographic separation (see U.S. Ser. No. 60/377052, filed May 1, 2002, Wyeth Case AM100862L1). The synthesis described herein eliminates the need for chromatography.

In the present invention exclusively one isomer is enzymatically cleaved effectively facilitating the separation of the desired intermediate carboxylic acid useful for the preparation of beta-lactamase inhibitors, from the second ester isomer.

As reported, in the preparation of beta-lactamase inhibitor, (5R,6Z)-6-(5,6-dihydro-4H-pyrrolo[1,2-b]pyrazol-2-yl-methylene)-7-oxo4-thia-1-azabicyclo[3.2.0]hept-2-ene-2-carboxylic acid, a key intermediate, 5,6-dihydro-4H-pyrrolo(1,2-b)pyrazole-2-carboxylic acid may be formed by chemical hydrolysis of a mixture of positional isomers or chromatographic separation of the individual positional isomers followed by chemical hydrolysis. However, after chemical hydrolysis of a mixture of isomers another difficult chromatographic separation to isolate 5,6-dihydro-4H-pyrrolo(1,2-b)pyrazole-2-carboxylic acid is required.

As described herein, 5,6-dihydro-4H-pyrrolo(1,2-b)pyrazole-2-carboxylic acid is selectively synthesized from a mixture of ester isomers by enzymatic hydrolysis of the desired ester in aqueous solvent. Separation of the esters by chemical methods could lead to non-selective hydrolysis of the undesired ester resulting in lower isomeric purity of the acid. In addition, enzymatic hydrolysis can eliminate crystallization steps. The isolated acid purity of 5,6-dihydro-4H-pyrrolo(1,2-b)pyrazole-2-carboxylic acid is greater than 99% and the yield by the described enzymatic process is at least 82%, and involves very simple process steps of separating the undesired ester by organic solvent extraction of the aqueous solvent, acidifying the aqueous solvent and isolating the insoluble acid by filtering. The simple process conditions and inexpensive enzyme increase the process efficiency for the preparation of 5,6-dihydro-4H-pyrrolo(1,2-b)pyrazole-2-carboxylic acid.

In particular this invention is a process for the enzymatic hydrolysis of a mixture of bicyclic heteroaryl-2-carboxylate 6 and bicyclic heteroaryl-3-carboxylate 5 of the formulae

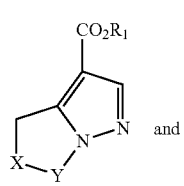 and

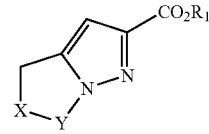

wherein Y is $(CH_2)n$; n is 1 or 2; X is —NR, O, S or —$CH_2$—; R is alkyl of 1 to 6 carbon atoms, or arylalkyl($C_1$ to $C_8$); where $R_1$ is alkyl of 1 to 6 carbon atoms; provided n is 2 when X is NR or O to selectively produce a bicyclic heteroaryl-2-carboxylic acid 7 of the formula

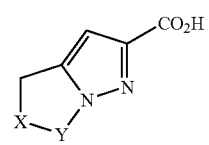

wherein X and Y are defined as above;

comprising:

a) contacting a mixture of bicyclic heteroaryl-2-carboxylate 6 and bicyclic heteroaryl-3-carboxylate 5 wherein X, Y and R are defined as above with an effective amount of a hydrolyzing enzyme in aqueous solvent at an effective pH range, for an effective time, optionally in a buffer and optionally in the presence of a cosolvent;

b) maintaining the pH at about 6.5 to about 7.8 by the addition of a base;

c) removing the bicyclic heteroaryl-3-carboxylate 5 by organic solvent extraction;

d) separating the aqueous solvent and optionally adjusting the pH from about 2.0 to about 3.0;

e) isolating the bicyclic heteroaryl-2-carboxylic acid 7 of the formula

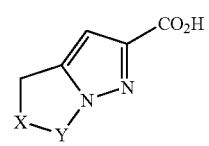

wherein X and Y are defined as above, as the free acid or as a pharmaceutically acceptable salt.

In particular, lipases, acylase and a protease enzyme show selectivity for the 5,6-dihydro-4H-pyrrolo(1,2-b)pyrazole-2-carboxylic acid ethyl ester over the 5,6-dihydro-4H-pyrrolo (1,2-b)pyrazole-3-carboxylic acid ethyl ester.

This invention further provides a process for the preparation of bicyclic heteroaryl carboxaldehydes 11 of the formula

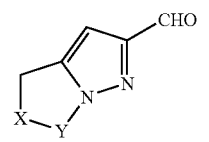

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;

which process comprises the steps of:
a. nitrosating an amino acid 1 of the formula

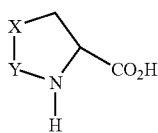

1 wherein X and Y are defined as above with a nitrosating reagent to form a nitroso compound of formula 2 wherein X and Y are defined as above

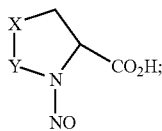

2 b. reacting the nitroso compound 2 with a dehydrating agent and neutralizing with inorganic base to form the ylide of formula 3 wherein X and Y are defined as above

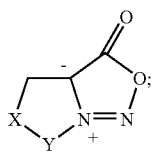

3 c. reacting the ylide of formula 3 with a propiolate ester of formula 4

HC≡CCO$_2$R$_1$    4 where $R_1$ is alkyl of 1 to 6 carbon atoms, in aprotic solvents to form a mixture of bicyclic-heteroaryl-3-carboxylic acid ester 5 and bicyclic-heteroaryl-2-carboxylic acid ester 6 wherein $R_1$, X and Y are defined as above

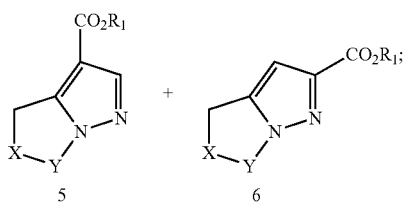

d. contacting the mixture of bicyclic-heteroaryl-3-carboxylic acid ester 5 and bicyclic-heteroaryl-2-carboxylic acid ester 6 with an effective amount of a hydrolyzing enzyme in aqueous solvent at an effective pH range, for an effective time, optionally in a buffer and optionally in the presence of a cosolvent;

e. maintaining the pH at about 6.5 to about 7.8 by the addition of a base;

f. removing the bicyclic heteroaryl-3-carboxylate 5 by organic solvent extraction;

g. separating the aqueous solvent and optionally adjusting the pH from about 2.0 to about 3.0;

h. isolating the bicyclic heteroaryl-2-carboxylic acid 7 or salt thereof of the formula

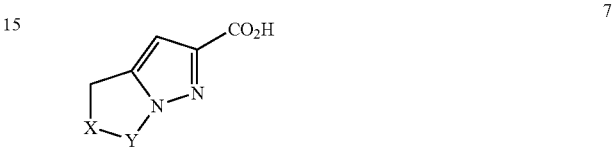

7 wherein X and Y are defined as above;

i. reacting the bicyclic-heteroaryl-2-carboxylic acid 7 or pharmaceutically acceptable salts thereof with an acid halide reagent or coupling reagent to form an activated intermediate 8 where Q is a leaving group formed from the coupling reagent or acid halide reagent and wherein X and Y are defined as above

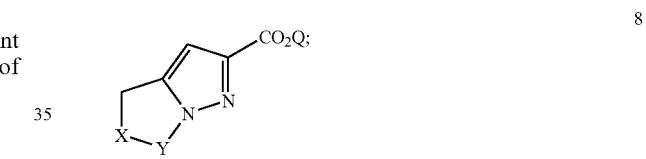

8 j. reacting activated intermediate 8 or bicyclic-heteroaryl-2-carboxylic acid 7 with a substituted hydroxylamine of the formula $R_3NHOR_2$ 9 where $R_2$ and $R_3$ are independently alkyl of 1 to 6 carbon atoms in the presence of an organic base to provide an amide of formula 10

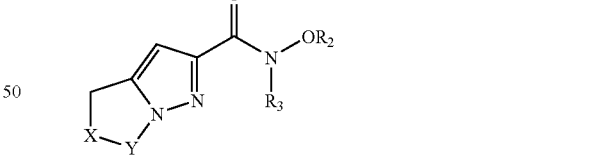

10 wherein X and Y are defined as above;

k. reducing the amide of formula 10 with a reducing agent to provide a bicyclic heteroaryl carboxaldehyde 11

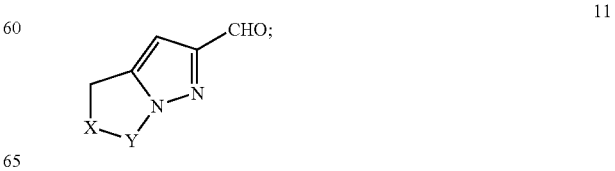

11 l. wherein X and Y are defined as above and isolating a bicyclic heteroaryl carboxaldehyde 11.

A further embodiment of this invention provides a process for the preparation of bicyclic heteroaryl carboxaldehydes 11

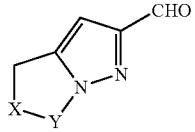

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;

which process comprises the steps of:
a. contacting a mixture of bicyclic-heteroaryl-3-carboxylic acid ester 5 and bicyclic-heteroaryl-2-carboxylic acid ester 6 wherein X and Y are defined as before and $R_1$ is alkyl of 1 to 6 carbon atoms

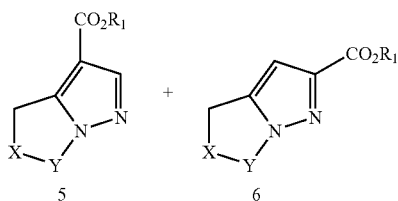

with an effective amount of a hydrolyzing enzyme in aqueous solvent at an effective pH range, for an effective time, optionally in a buffer, and optionally in the presence of a cosolvent;
b. maintaining the pH at about 6.5 to about 7.8 by the addition of a base;
c. removing the bicyclic heteroaryl-3-carboxylate 5 by organic solvent extraction;
d. separating the aqueous solvent and optionally adjusting the pH from about 2.0 to about 3.0;
e. isolating the bicyclic heteroaryl-2-carboxylic acid 7 of the formula

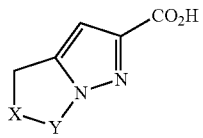

wherein X and Y are defined as above or pharmaceutically acceptable salts thereof;
f. reacting the bicyclic heteroaryl-2-carboxylic acid 7 or salts thereof with an acid halide reagent or coupling reagent to form an activated intermediate 8 where Q is a leaving group formed from the coupling reagent or acid halide reagent and X and Y are defined above

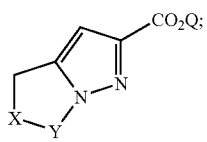

g. reacting an activated intermediate 8 or the bicyclic-heteroaryl-2-carboxylic acid 7 with a substituted hydroxylamine of the formula $R_3NHOR_2$ 9 where $R_2$ and $R_3$ are independently alkyl of 1 to 6 carbon atoms in the presence of an organic base to provide an amide of formula 10

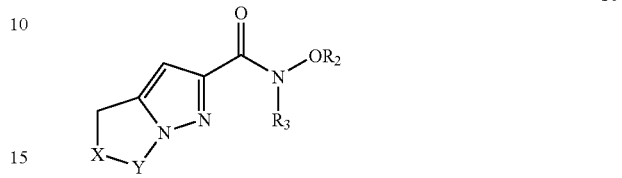

wherein X, Y, $R_2$ and $R_3$ are defined as above;
h. reducing the amide of formula 10 with a reducing agent to provide a bicyclic heteroaryl carboxaldehyde of formula 11

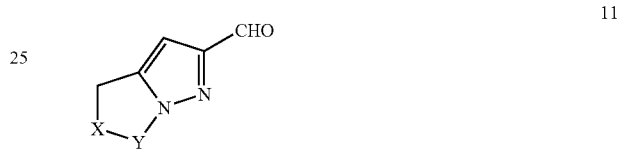

wherein X and Y are defined as above and isolating a bicyclic heteroaryl carboxaldehyde of formula 11.

This invention further provides a process for the preparation of a bicyclic heteroaryl penem-2-carboxylic acid 16, protected acid, pharmaceutically acceptable salt or preferably alkali metal salt of the formula

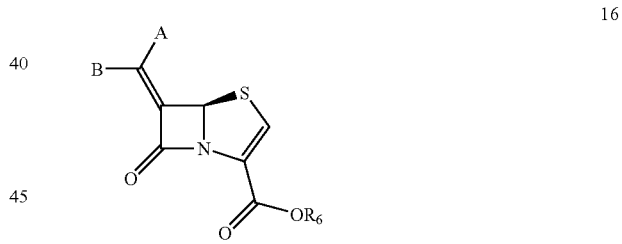

wherein:
one of A and B denotes hydrogen and the other a moiety

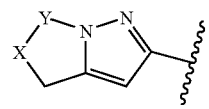

Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;
$R_3$ is alkyl of 1 to 6 carbon atoms;
$R_6$ is H, an in vivo hydrolyzable ester selected from the group $C_1$-$C_6$ alkyl, $C_5$-$C_6$ cycloalkyl, $CHR_3OCOC_1$-$C_6$ or a pharmaceutically acceptable salt thereof or preferably an alkali metal salt;

which process comprises the steps of:
a. nitrosating an amino acid 1 of the formula

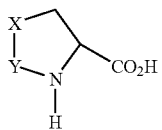

1 wherein X and Y are defined as above with a nitrosating reagent to form a nitroso compound of formula 2 wherein X and Y are defined as above

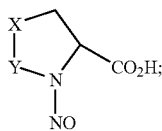

2 b. reacting the nitroso compound 2 with a dehydrating agent and neutralizing with inorganic base to form the ylide of formula 3 wherein X and Y are defined as above

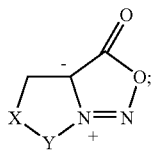

3 c. reacting the ylide of formula 3 with a propiolate ester of formula 4

$HC{\equiv}CCO_2R_1$     4 where $R_1$ is alkyl of 1 to 6 carbon atoms, in aprotic solvents to form a mixture of bicyclic-heteroaryl-3-carboxylic acid ester 5 and bicyclic-heteroaryl-2-carboxylic acid ester 6 wherein $R_1$, X and Y are defined as above

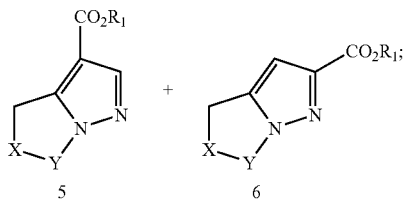

5     6 d. contacting the mixture of bicyclic-heteroaryl-3-carboxylic acid ester 5 and bicyclic-heteroaryl-2-carboxylic acid ester 6 wherein X, Y and $R_1$ are defined as above with an effective amount of a hydrolyzing enzyme in aqueous solvent at an effective pH range, for an effective time, optionally in a buffer, and optionally in the presence of a cosolvent;
e. maintaining the pH at about 6.5 to about 7.8 by the addition of a base;
f. removing the bicyclic heteroaryl-3-carboxylate 5 by organic solvent extraction;

g. separating the aqueous solvent and optionally adjusting the pH from about 2.0 to about 3.0;
h. isolating the bicyclic heteroaryl-2-carboxylic acid 7 of the formula

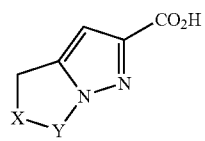

7 wherein X and Y are defined as above;
i. reacting the bicyclic-heteroaryl-2-carboxylic acid 7 or pharmaceutically acceptable salts thereof with an acid halide reagent or coupling reagent to form an activated intermediate of formula 8 where Q is a leaving group formed from the coupling reagent or acid halide reagent wherein X and Y are defined as above

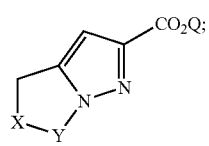

8 j. reacting an activated intermediate of formula 8 or the bicyclic-heteroaryl-2-carboxylic acid 7 with a substituted hydroxylamine of the formula $R_3NHOR_2$ 9 where $R_2$ and $R_3$ are independently alkyl of 1 to 6 carbon atoms in the presence of an organic base to provide an amide of formula 10 wherein X, Y, $R_2$, and $R_3$ are defined as above

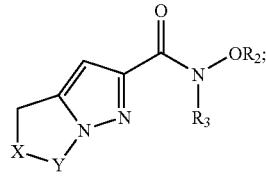

10 k. reducing the amide of formula 10 with a reducing agent to provide a bicyclic heteroaryl carboxaldehyde of formula 11 wherein X, Y, $R_2$ and $R_3$ are defined as above

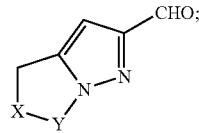

11 l. condensing the bicyclic heteroaryl carboxaldehyde 11 with bromo-penem 13 where $R_6$ is an in vivo hydrolyzable ester selected from the group $C_1$-$C_6$ alkyl, $C_5$-$C_6$ cycloalkyl, and $CHR_3OCOC_1$-$C_6$ or additionally a benzyl or p-nitrobenzyl protecting group, of the formula

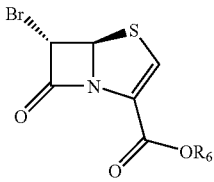

in the presence of a Lewis acid, etherate and a mild base to form an aldol 14 of the formula wherein X, Y and $R_6$ are defined as above

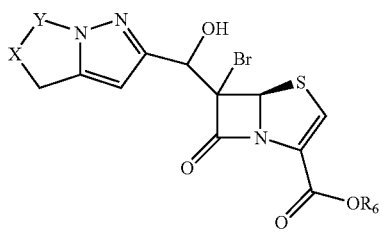

m. reacting aldol 14 with an acid chloride or anhydride, $(R_4)Cl$ or $(R_4)_2O$, or with tetrahalomethane, $C(X_1)_4$, and triphenyl phosphine, to form intermediate compound 15 wherein $R_4$ is alkyl$SO_2$, aryl$SO_2$, alkylCO, or arylCO; $X_1$ is Br, I, or Cl; X, Y and $R_6$ are as defined above; and $R_5$ is $X_1$ or $OR_4$; and

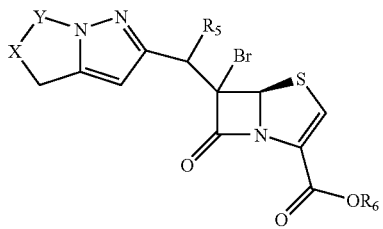

n. converting the intermediate compound 15 by a reductive elimination process to the bicyclic-heteroaryl-penem-2-carboxylic acid 16 where $R_6$ is H, and if desired converting to a pharmaceutically acceptable salt, preferably an alkali metal salt or to an ester wherein $R_6$ is $C_1$-$C_6$ alkyl, $C_5$-$C_6$ cycloalkyl, and —$CHR_3OCOC_1$-$C_6$, of the formula

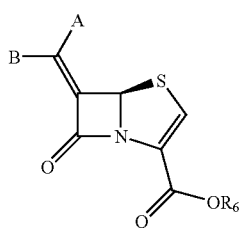

and isolating the bicyclic-heteroaryl-penem-2-carboxylic acid 16.

DESCRIPTION OF THE PREFERRED EMBODIMENTS

Figure 2:
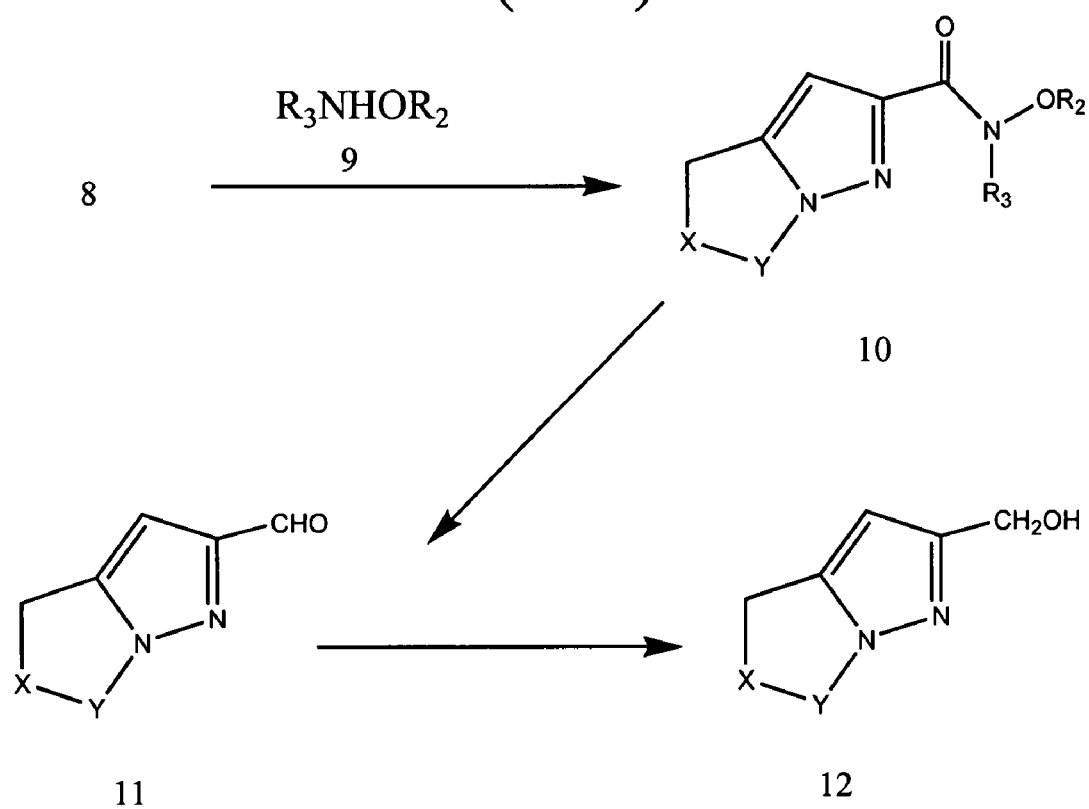

As described in Scheme I, (FIG. 1 and FIG. 2), amino acid 1 (L, D or racemic) where X, Y, R and n are hereinbefore described are nitrosated in the presence of a nitrosating reagent which includes sodium nitrite and hydrochloric acid to afford 1-nitroso-amino acid 2 which is further reacted with a dehydrating agent which includes but not limited to trifluoroacetic anhydride by using the described method (Ranganathan, D.; Shakti, B. "A Novel Proline Derived Meso-Ionic Synthon." Tetrahedron Letts. 1983: 24 (10); 1067-1070) with work-up modifications which include neutralization of trifluoroacetic acid formed in the reaction mixture with an aqueous solution of an inorganic base such a potassium bicarbonate, or potassium carbonate (and the like) or an anhydrous inorganic base such as powdered potassium carbonate and extraction of the desired product with a solvent such as dichloromethane, which eliminates the need for chromatography, to prepare ylide 3. Reaction of ylide 3 with propiolate esters 4 where $R_1$ is alkyl of 1 to 6 carbon atoms, such as ethyl propiolate using the method (Ranganathan, D.; Shakti, B. "A Novel Proline Derived Meso-Ionic Synthon." Tetrahedron Letts. 1983: 24 (10); 1067-1070), preferably methyl or ethyl, in aprotic solvents, which include substituted aromatic hydrocarbons, (e.g. chlorobenzene, mesitylene and the like), substituted amides (e.g. N,N-dimethylformamide, N,N-dimethylacetamide and the like), sulfoxides (e.g. dimethyl sulfoxide and the like) and ethers (e.g. ethers of ethylene glycol such as 1,2-diethyl, 1,2-dimethyl and the like) affords a mixture of bicyclic-heteroaryl-3-carboxylic acid ester 5 and bicyclic-heteroaryl-2-carboxylic acid ester 6 wherein $R_1$, X and Y are as defined above. Preferred reaction temperatures are in the range of about 100-165° C. Preferred solvents are ethers of ethylene glycol (diethyl, dimethyl and the like) substituted amides (N,N-dimethylformamide) and substituted aromatic hydrocarbons such as chlorobenzene in which a mixture of esters with a ratio favoring the desired bicyclic-heteroaryl-2-carboxylic acid ester 6, are formed in a range of about 1.5:1 to about 3:1. Especially preferred solvents include diethyl ethylene glycol (1,2-diethoxyethane, DEE) or chlorobenzene wherein the reaction is complete in about 8-12 hours at a reaction temperature of about 120-125° C. and provides a mixture of bicyclic-heteroaryl-2-carboxylic acid ester 6 and bicyclic-heteroaryl-3-carboxylic acid ester 5, in a ratio in the range of about 1.5:1 to about 2.5:1 in a ratio favorable to the desired bicyclic-heteroaryl-2-carboxylic acid ester 6, with little contamination from polymeric materials.

A mixture of bicyclic-heteroaryl-2-carboxylic acid ester 6 and bicyclic-heteroaryl-3-carboxylic acid ester 5 is contacted with hydrolyzing enzymes and the bicyclic-heteroaryl-2-carboxylic acid ester 6 selectively hydrolyzed over the bicyclic-heteroaryl-3-carboxylic acid ester 5 to afford bicyclic-heteroaryl-2-carboxylic acid 7 wherein X and Y are as defined above. Hydrolyzing enzymes, include lipases, acylase, protease and esterases. The hydrolyzing enzyme is first dissolved in aqueous solvent optionally buffered within a preferable pH range of 6.5 to 7.8. For enzyme activity, the preferred pH is within the effective pH range that facilitates the active state of the particular enzyme being used having the ability to hydrolyze the ester. Hydrolyzing enzymes include: lipases, esterase, acylase and a protease. Preferred buffers are Tris-HCl buffer, potassium phosphate buffer, or other buffer at about pH 7.25. The concentration of enzyme in aqueous solvent may vary over a range such as 3 mg to 10 mg/ml with a value of about 6 mg/ml being typical. A cosolvent may optionally be added. Cosolvents include acetonitrile and N,N-dimethyl formamide preferably, 10% acetonitrile. Acetonitrile as cosolvent is tested from zero to 30% in the enzyme reaction mix for its effect. Acetonitrile helps better distribute the ester mix in the aqueous reaction system. Results indicate that acetonitrile does not affect the enzyme selectivity however, if above 10% concentration and only slightly slowed down the enzyme reaction rate. When crude ester mix after the chemical synthesis without further purification is used in the enzyme reaction, addition of acetonitrile at 10% (final concentration) to the reaction assists in the uniform distribution of the ester substrate, without any negative effect on the enzyme activity and selectivity. Since an immobilized enzyme preparation is used, at the end of the reaction, separation of the enzyme is easy. An effective pH range may be about 4.0 to about 10.0. However, should the pH of the enzyme hydrolysis reach 5.0 or lower the enzyme activity may be inhibited and result in incomplete substrate hydrolysis. As the reaction proceeds the pH is maintained at about 7.0 preferably in the range about 6.5 to about 7.8 by the addition of a base and in particular a solution of sodium hydroxide, or optionally with ammonium hydroxide and the like. The enzyme reaction time varies from about 9 to 72 hours, depending on the type of hydrolyzing enzyme and the substrate concentration used in the reaction mixture. The extent of the substrate hydrolysis is monitored by HPLC or by monitoring the consumption of alkali to maintain the pH of the reaction at about 7.0. The extent of the desired ester hydrolysis does not affect the isomeric purity of the desired acid product however, if the substrate ester hydrolysis is incomplete, only a lower yield of the acid product will result. Purification of bicyclic-heteroaryl-2-carboxylic acid 7 from unhydrolyzed ester bicyclic-heteroaryl-3-carboxylic acid ester 5 is easily accomplished through organic solvent extraction of unhydrolyzed ester. Suitable organic solvents include: ethyl acetate, isopropyl acetate, t-butyl acetate, diethyl ether, isopropyl ether, or any other water-immiscible organic solvent in which the unhydrolyzed esters are soluble, preferably ethyl acetate. The bicyclic heteroaryl-2-carboxylic acid 7 may be isolated by lyophilization or evaporation of the separated aqueous phase. The bicyclic heteroaryl-2-carboxylic acid 7 may optionally be isolated after adjusting the pH of the separated aqueous phase from about 2.0 to about 3.0 with mineral acid, preferably hydrochloric acid.

As further described in Scheme I (FIG. 1 and FIG. 2), conversion of bicyclic-heteroaryl-2-carboxylic acid 7 optionally as its alkali metal salts (sodium, potassium, lithium and the like) to an activated intermediate 8 is accomplished in several ways. Preferably, reaction of bicyclic-heteroaryl-2-carboxylic acid 7 with acid halide reagents $SO_2Q_2$ or QCOCOQ where Q is chloro or bromo such as oxalyl chloride, thionyl chloride, thionyl bromide and the like in an appropriate aprotic solvent (such as dichloromethane, 1,2-dichloroethane, toluene, dimethoxyethane and the like) preferably in the presence of an N,N-dialkylamide catalyst such as N,N-dimethylformamide at an appropriate temperature (−10-30° C.) affords activated intermediate 8 where Q is chloro or bromo. The activated intermediate 8 thus generated is reacted with a substituted hydroxylamine $R_3NHOR_2$ 9 where $R_2$ and $R_3$ are independently alkyl of 1 to 6 carbon atoms [i.e. $R_3NHOR_2$, wherein $R_3$, $R_2$=Me, i.e. O,N-dimethylhydroxylamine and the like] in a suitable solvent such as dichloromethane, toluene, dimethoxyethane and the like, in the presence of an organic base such as triethylamine, N,N-diisopropylethylamine, pyridine and the like, in a temperature range of about −10-50° C., to provide amide 10 wherein X, Y, $R_2$ and $R_3$ are defined as above. A preferred method involves generating the activated intermediate 8 where Q is Cl with oxalyl chloride in dichloromethane at about 0-25° C. in the presence of a catalytic amount of N,N-dimethylformamide and then reacting the activated intermediate 8 where Q is Cl with a sustituted hydroxylamine hydrochloride 9 in the presence of pyridine or N,N-diisopropylethylamine in the temperature range of about 0-25° C. to afford amide 10 wherein X, Y, $R_2$ and $R_3$ are defined as above.

Alternatively, the activated intermediate 8 where Q is Cl or Br may be reacted with substituted hydroxylamine hydrochloride 9 in a two phase system such as dichloromethane, toluene, ethyl acetate and the like and water in the presence of an inorganic base such as sodium hydroxide, sodium carbonate, sodium bicarbonate or potassium hydroxide, potassium carbonate, potassium bicarbonate and the like. An especially preferred method for forming the amide 10 wherein X, Y, $R_2$ and $R_3$ are defined as above, is to use Schotten-Baumen conditions in which a solution of the activated intermediate 8 of 2-carboxylic acid where Q is Cl in dichloromethane (generated from thionyl chloride/N,N-dimethylformamide) is reacted with an aqueous solution of substituted hydroxylamine 9 in the presence of an inorganic base, preferably potassium carbonate, in the temperature range of about 10-20° C. In particular, N-methoxy-N-methyl-5,6-dihydro-4H-pyrrolo[1,2-b]pyrazole-2-carboxamide is prepared by Schotten-Baumen conditions without requiring further purification after isolation.

Coupling of a bicyclic-heteroaryl-2-carboxylic acid 7, which includes 5,6-dihydro-4H-pyrrolo[1,2-b]pyrazole-2-carboxylic acid, with a substituted hydroxylamine, 9 Scheme I (FIG. 1 and FIG. 2), to synthesize an amide 10 wherein X, Y, $R_2$ and $R_3$ are defined as above can be accomplished using several procedures.

In a typical coupling procedure, the bicyclic-heteroaryl-2-carboxylic acid 7 and substituted hydroxylamine 9 are reacted with a suitable coupling reagent. A suitable coupling reagent converts the carboxylic acid group into a activated intermediate 8 where Q is a leaving group formed from the coupling reagent, such that an amide linkage is formed between the carboxylic acid and the substituted hydroxylamine.

Examples of suitable coupling reagents include 1-(3-dimethylaminopropyl)-3-ethylcarbodiimide hydrochloride-hydroxybenzotriazole (DEC/HBT), carbonyldiimidazole, carbonyldimidazole/hydroxybenzotriazole dicyclohexylcarbodiimide/HBT, dicyclohexylcarbodiimide/N-hydroxysuccinimide, 2-ethoxy-1-ethoxycarbonyl-1,2-dihydroquinoline (EEDQ), 2-chloro-1-methylpyridinium iodide, diphenylphosphinyl chloride (DPPCl), propanephosphonic anhydride (propanephosphonic acid anhydride, PAA), diethylphosphoryl cyanide, phenyldichlorophosphate plus imidazole, benzotriazol-1-yloxytris(dimethylamino)phosphonium hexafluorophosphate (BOP-reagent), N,N'bis[2-oxo-3-oxazolidinyl]phosphorodiamidic chloride (BOB Cl), 2-(1H-benzotriazole-1-yl)-1,1,3,3-tetramethyluronium tetrafluoroborate, 2-(1H-benzotriazole-1-yl)-1,1,3,3-tetramethyluronium hexafluorophosphate, bromo-tris-pyrrolidino-phosphonium hexafluorophosphate and benzotriazole-1-yloxy-tris-pyrrolidino-phosphonium hexafluorophosphate. The coupling reaction may optionally be in several steps or in a telescoped process.

A typical coupling reaction is generally performed in an inert solvent, preferably an aprotic solvent at a temperature of about −20° C. to about 50° C. for about 1 to about 48 hours, optionally in the presence of a tertiary amine such as, N,N-diisopropylethylamine, N-methylmorpholine, N-methylpyrrolidine, triethylamine, 4-dimethylaminopyridine, 2,6-di-tert-butyl-4-methylpyridine, pyridine and the like. Suitable solvents include acetonitrile, dichloromethane, ethyl acetate, dimethylformamide, tetrahydrofuran, dioxane or chloroform or mixtures thereof.

In an example of a multistep coupling process, the bicyclic-heteroaryl-2-carboxylic acid 7 is reacted with a coupling reagent to form an activated intermediate 8, which may optionally be isolated, where Q is a leaving group. In a second step, the activated intermediate 8 is then reacted with the substituted hydroxylamine 9 to form the amide 10. Further examples of coupling reagents that convert an acid to an activated intermediate include thionyl chloride, thionyl bromide, oxalyl chloride, cyanuric fluoride, which forms acid fluorides (Q is F), or an alkyl chloroformate such as isobutyl or isopropenyl chloroformate (in the presence of a tertiary amine base), forming a mixed anhydride of the carboxylic acid. An additional example of a coupling reagent for preparing mixed anhydrides is 2,4,6-trichlorobenzoyl chloride [Inanaga et al. Bull. Chem. Soc. Jpn. 52, 1989 (1979)]. The coupling reaction is generally performed in an inert solvent, preferably an aprotic solvent at a temperature of about −20° C. to 30° C. for about 1 to about 24 hours, optionally in the presence of a tertiary amine such as, N,N-diisopropylethylamine, N-methylmorpholine, N-methylpyrrolidine, triethylamine, 4-dimethylaminopyridine, 2,6-di-tert.-butyl-4-methylpyridine, pyridine and the like. Suitable solvents include acetonitrile, dichloromethane, ethyl acetate, dimethylformamide, tetrahydrofuran, dioxane or chloroform or mixtures thereof. The second step for coupling of the activated intermediate 8 has been described hereinbefore wherein the activated intermediate is prepared from a salt of the carboxylic acid. In the second step when the activated intermediate is a mixed anhydride the amine in a suitable solvent, hereinbefore defined, is added to the solution of the mixed anhydride, in the presence of a suitable base, hereinbefore defined, at the temperature used for activation and the temperature is slowly adjusted to about 30° C. The amine is added to the solution at the temperature used for activation and the temperature is slowly adjusted to about 30° C. The reaction time is about 1-48 h.

Other examples of coupling reagents which convert a carboxylic acid to an activated intermediate, optionally isolated, such as an activated ester, include pentafluorophenyl trifluoroacetate which provides an activated phenolic ester. In particular, simple esters such as methyl, ethyl and propyl, prepared by reaction of 5,6-dihydro-4H-pyrrolo[1,2-b]pyrazole-2-carboxylic acid with the corresponding alcohols using conventional methods, may also serve as activated intermediates. Coupling reagents that provide an activated intermediate, such as, an acyl azide further include diphenylphoshoryl azide. Coupling reagents that provide an activated intermediate, such as, an acyl cyanide include diethylphosphoryl cyanide.

The coupling reaction is in general carried out between about −30° C. and 60° C. conveniently at or below 0° C. In the second step, the substituted hydroxylamine is added to the solution of activated intermediate at the temperature used for activation and the temperature is slowly adjusted to about 30° C. The reaction time is about 1-96 h. Additional coupling reagents are hereinbefore defined.

Reducing the amide 10 wherein X, Y, $R_2$ and $R_3$ are defined as above to produce the bicyclic heteroaryl carboxaldehyde, 11 may be effected with a reducing agent which includes an excess of hydride reagents, such as lithium aluminum hydride and disobutyl aluminum hydride [DIBAL (H)] in solvents, such as tetrahydrofuran, ether and toluene at temperatures between about −10 and 25° C. The use of lithium aluminum hydride in tetrahydrofuran at temperatures in the range of about 0-25° C. is preferred. An especially preferred method is described wherein the reducing reagent is lithium aluminum hydride [0.5 mol per mol. of amide] and the reaction solvent is tetrahydrofuran. The reaction temperature is kept at about 0-5° C. for about 18 hours. To reduce the quantity of a biproduct, alcohol 12, generated on quenching the reaction mixture with water, the reaction mixture is preferentially, quenched by adding the reaction mixture to a solution of tetrahydrofuran and water. Acid extraction with dichloromethane is preferred. Especially preferred is purification of the bicyclic heteroaryl carboxaldehyde, 11 via a water soluble, sodium bisulfite complex which in particular effectively removes residual alcohol 12.

Figure 3:
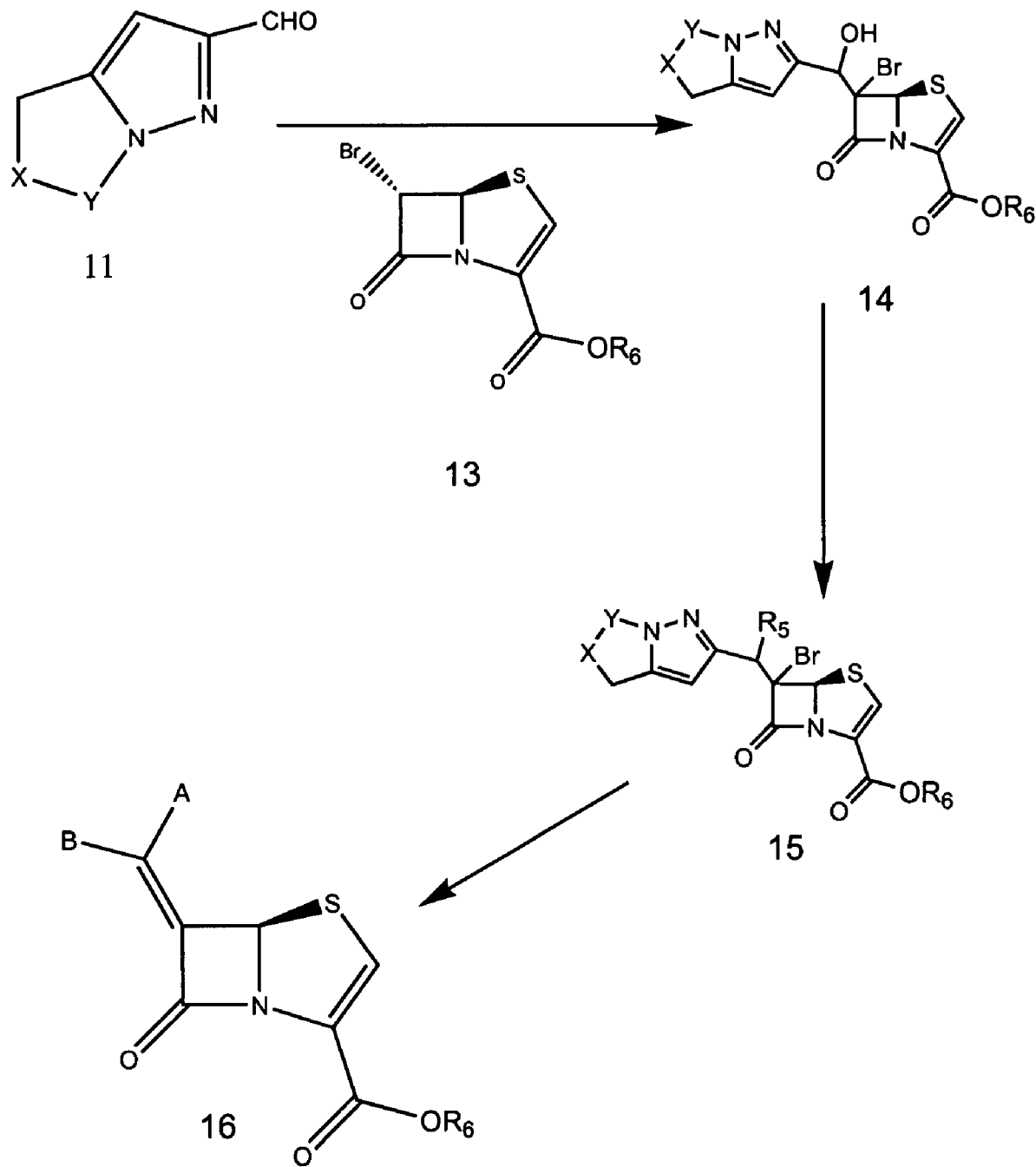

As further described in Scheme II, (FIG. 3), bicyclic-heteroarylpenem-2-carboxylic acid 16, protected acid or pharmaceutically acceptable salt thereof, preferably an alkali metal salt where, one of A and B denotes a hydrogen and the other a moiety

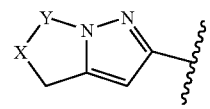

wherein X and Y are defined as above, can be prepared by condensing bicyclic heteroaryl carboxaldehydes 11 prepared as described in Scheme I (FIG. 1 and FIG. 2), with 6-bromopenem 13 having a protected acid where $R_6$ is an in vivo hydrolyzable ester selected from the group $C_1$-$C_6$ alkyl, $C_5$-$C_6$ cycloalkyl, and —$CHR_3OCOC_1$-$C_6$ or additionally benzyl or p-nitrobenzyl protecting groups in the presence of a Lewis acid, preferably anhydrous magnesium halide (Br or Cl), more preferably anhydrous $MgBr_2$ or $MgBr_2$: etherate and a mild base such as triethylamine, dimethylaminopyridine (DMAP), or diisopropyl ethyl amine, at low temperature preferably at about −20° C. to −40° C. to afford aldol 14 which can be functionalized with acid chlorides or anhydrides preferably to an acetate, triflate or a tosylate or optionally can be converted to a halogen derivative by reaction with tetrahalomethane and triphenyl phosphine at room temperature in a suitable organic solvent preferably $CH_2Cl_2$ to give intermediate 15. Reacting aldol 14 with an acid chloride or anhydride, $(R_4)Cl$ or $(R_4O$, or with tetrahalomethane, $C(X_1)_4$, and triphenyl phosphine, forms intermediate compound 15 wherein $R_4$ is alkyl$SO_2$, alkylCO, or arylCO; $X_1$ is Br, I, or Cl; A and R are as defined above; and $R_6$ is $X_1$ or $OR_4$. The intermediate 15 can be converted to the desired bicyclic-heteroaryl-penem-2-carboxylic acid 16, protected acid, or pharmaceutically acceptable salt thereof, preferably an alkali metal salt by a reductive elimination process using a metal such as activated zinc and phosphate buffer at mild temperatures preferably about 20° C. to 35° C. at a pH of about 6.5 to 8.0 or hydrogenating over a catalyst preferably palladium on charcoal. It should be noted that the reductive elimination step could be conducted such that deprotection of the carboxyl group occurs. If the protecting group on the carboxylate oxygen is para-nitrobenzyl substituent then the reductive elimination and deprotection can be achieved by a single step. However if the protecting group is other than para-nitrobenzyl substituent, a two step procedure can be followed depending up on the nature of the protecting group. The product can be isolated as a free acid or a pharmaceutically acceptable salt, preferably as an alkali metal salt. The above mentioned two step procedure can be carried out in one step by carrying out the entire process without isolating the intermediate 15. Additionally, the free acid or alkali metal salt may be converted to an ester where $R_6$ is $C_1$-$C_6$ alkyl, $C_5$-$C_6$ cycloalkyl, and —$CHR_3OCOC_1$-$C_6$.

In this disclosure a number of terms are used and the following definitions are provided.

Aryl, as used herein refers to an aromatic hydrocarbon moiety of 6-12 carbon atoms.

As used herein, the term, $C_5$-$C_6$ cycloalkyl refers to a monocyclic saturated ring having 5 to 6 carbon atoms. Exemplary cycloalkyl rings include cyclopentyl, or cyclohexyl.

As used herein, the term aqueous solvent means water.

As used herein, the term "reacting" is intended to represent bringing the chemical reactants together under conditions such to cause the chemical reaction indicated to take place.

The term "leaving group" generally refers to groups readily displaceable by a nucleophile, such as an amine. Such leaving groups are well known in the art. Examples of such leaving groups include, but are not limited to, N-hydroxysuccinimide, N-hydroxybenzotriazole, fluorine, chlorine, bromine, 1,1'-carbonyldiimidazole and the like.

As used herein, contacting is intended to represent bringing the ester reactants together in an aqueous medium in the presence of a hydrolyzing enzyme such to allow the enzymatic reaction to take place.

As used herein, the term hydrolyzable ester designates any ester conventionally used for protecting carboxylic acids which can be hydrolyzed with a hydrolyzing enzyme described herein.

As used herein, effective hydrolyzing enzyme means an enzyme that can generate a detectable amount of carboxylic acid product from an ester reactant or mixture of ester reactants. Effective hydrolyzing enzymes are selected from the group lipase, esterase, acylase or a protease. Specific examples include *C. antarctica* lipase B, *Aspergillus*, acylase, *Aspergillus oryzae* protease M, *C. rugosa* lipase, and lipase from a *Pseudomonas* sp.

As used herein, an effective amount of an effective hydrolyzing enzyme, means the amount of enzyme that can generate the detectable amount of acid product from the ester substrate. In general, the effective amount is in the range of about 3 mg to 10 mg/ml and preferably about 6 mg/ml.

As used herein, the effective pH range for enzyme reaction is that pH at which the given enzyme shows the catalytic activity on the ester substrate. The pH range varies and depends on the particular enzyme used. For example, for a lipase the effective pH range is about from 5.0 to 10.0. Similarly, for a protease the effective pH range is about pH 4.0 to 10.0 and for acylase, the effective pH range is about 5.0 to 10.0. A preferred pH range is about 6.5 to about 7.8. Also preferred is a pH range of about 7.2 to about 7.5. More preferred is a pH of about 7.0.

As used herein, the effective temperature of the enzyme reaction is the temperature at which the given enzyme shows the activity on the given substrate. For example, the temperature is generally from about 20° C. to about 65° C., depending on the enzyme used. Preferably, the effective temperature is about 37° C.

As used herein enzymatically selective refers to a reaction wherein one functional group (e.g., a ester group) can be substituted on a molecule at different positions (positional isomers) and reaction occurs selectively at only one of the positions.

As used herein, the effective time for the enzymatic hydrolysis which is about 9 to 72 hours.

As used herein, the pharmaceutically acceptable salts of the basic compounds prepared the processes of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where a carboxyl group is present, salts of the compounds prepared by the processes of this invention may be formed with bases such as alkali metals (Na, K, Li) or alkaline earth metals (Ca or Mg).

As used herein, mineral acids mean sulfuric acid, hydrochloric acid and the like.

The invention will now be described in more detail in the following examples which are given by way of illustration and are not intended to limit the invention.

EXPERIMENTAL METHODS

General Enzymatic Conditions

The mixture of esters, 5,6-dihydro-4H-pyrrolo(1,2-b)pyrazole-2-carboxylic acid ethyl ester and 5,6-dihydro-4H-pyrrolo(1,2-b)pyrazole-3-carboxylic acid ethyl ester are tested in 1 ml reactions for screening enzyme activity and the reactions are analyzed by high pressure liquid chromatography (HPLC). Typically, the substrate concentration ranged from 1 mg to 20 mg/ml in 0.1M potassium phosphate buffer pH 7.25 containing 5 to 10 mg of enzyme or 10 μl if it is a liquid. The reactions are incubated at 37° C. overnight. When the ester is hydrolyzed, it is indicated by a drop in the initial pH of the reaction to about 6.0. HPLC Conditions: Samples are analyzed on Waters HPLC (Alliance HT:2795) using a Waters™ Symmetry™ C18 column 3.5 m; 4.6× 75mm) and the following solvent gradient. Solvent A: 5% acetonitrile, 10 mM ammonium acetate in water; Solvent B: 80% acetonitrile, 10 mM ammonium acetate in water. Gradient conditions are; 90% A:10% B to 60% A:40% B in 10 minutes; 100% B in 15 minutes; continue with 100% B up to 20 minutes and switch back to 90% A:10% B. The compounds were detected at 215 or 226 nm. Flow rate was 1 ml/min. Different enzymes tested are listed in Table 1. Of the enzymes tested, an acylase from an *Aspergillus* sp. and lipases from *Pseudomonas* sp. and *Candida antarctica* showed selective hydrolysis of the desired ester, forming the desired acid isomer. Esterases from pig liver showed non-selective hydrolysis of both isomers.

TABLE 1

List of enzymes tested against the ester mixture of 5,6-dihydro-4H-pyrrolo(1,2-b)pyrazole-2-carboxylic acid ethyl ester * and 5,6-dihydro-4H-pyrrolo(1,2-b)pyrazole-3-carboxylic acid ethyl ester **

| Entry | Enzyme | Ester Hydrolysis |
|---|---|---|
| 1 | Lipase A "Amano" 12 | No |
| 2 | Lipase AK *Pseudomonas fluorescens* | No |
| 3 | Lipase AY - *Candida rugosa* crude enzyme | No |
| 4 | Lipase BC - *Pseudomonas* sp | No |
| 5 | Lipase F-AP15 | No |

TABLE 1-continued

List of enzymes tested against the ester mixture of 5,6-dihydro-4H-pyrrolo(1,2-b)pyrazole-2-carboxylic acid ethyl ester * and 5,6-dihydro-4H-pyrrolo(1,2-b)pyrazole-3-carboxylic acid ethyl ester **

| Entry | Enzyme | Ester Hydrolysis |
|---|---|---|
| 6 | Lipase G 50- | No |
| 7 | Lipase M 10- | No |
| 8 | Lipase PS - *Pseudomonas cepacia* | No |
| 9 | Lipase R Amano G- | No |
| 10 | Lipase TypeVII-(crude) *Candida rugosa* | No |
| 11 | Lipozyme RMIM - *R. meihei* | No |
| 12 | Lipozyme TLIM - *T. lanuginosa* | No |
| 13 | Newlase F | No |
| 14 | Novozyme435 - *C. antarctica* LipaseB | * hydrolyzed |
| 15 | Novozym 388 | No |
| 16 | Novozyme 398 | No |
| 17 | Alcalase - *Bacillus* protease | No |
| 18 | Acylase Amano - *Aspergillus* sp. | * hydrolyzed |
| 19 | Acid protease II | No |
| 20 | Acid protease A | No |
| 21 | Chirazyme P1 - *B. licheniformis* protease | No |
| 23 | Protease A-2G | No |
| 24 | Protease M | * hydrolyzed |
| 25 | Protease N | No |
| 26 | Protease P | No |
| 27 | Protease S | No |
| 28 | Chirazyme(Lipases) Screening Kit | |
| 29 | Lipase L-2 *C. antarctica* LipaseB soluble form. | * and ** hydrolyzed |
| 30 | L-3; crude *C. rugosa* | No |
| 31 | L-3 purified - *C. rugosa* | * hydrolyzed |
| 32 | L-5; LipaseA of *C. antarctica* | No |
| 34 | L-6; *Pseudomonas* sp. | * hydrolyzed |
| 35 | L-7; Pig pancreas | No |
| 36 | L-8; *T. lanuginosus* | No |
| 37 | L-9; *M. meihei* | No |
| 38 | L-10; *Alcaligenes* | No |
| 39 | Esterase E1 - Pig liver | * and ** hydrolyzed |
| 40 | Esterase E2 - Pig liver | * and ** hydrolyzed |

Example 1

Ester Hydrolysis with a Fungal Acylase

An acylase that hydrolyzes the N-acetyl amino acid derivatives to the corresponding amino acids is tested against the ester substrate mix. The reaction mix contains about 8.5 mg acylase (about 255 acylase units), 0.15 mM cobalt chloride in 1 ml potassium phosphate buffer pH about 7.0. To this about 10 mg of substrate ester mix is added and incubated at 37° C. The progress of the enzyme reaction is monitored by analyzing a small sample by HPLC. The desired ester isomer 5,6-dihydro-4H-pyrrolo(1,2-b)pyrazole-2-carboxylic acid ethyl ester is hydrolyzed by the enzyme and 5,6-dihydro-4H-pyrrolo(1,2-b)pyrazole-3-carboxylic acid ethyl ester is not hydrolyzed.

Example 2

Hydrolysis with Lipase from *Pseudomonas* sp.

Based on the general enzymatic conditions described above, 1.50 g of mixed esters, 5,6-dihydro-4H-pyrrolo(1,2-b)pyrazole-2-carboxylic acid ethyl ester and 5,6-dihydro-4H-pyrrolo(1,2-b)pyrazole-3-carboxylic acid ethyl ester is hydrolyzed with about 100 mg of *Pseudomonas* sp. Lipase (L-6) in 50 ml 0.1M potassium phosphate buffer pH 7.25 to which, 0.5 ml acetonitrile is added for even distribution of the substrate in the buffer. The reaction is mixed at 37° C. The acid released after enzyme hydrolysis lowers the reaction pH. Periodically pH of the reaction is checked and if it is 7.0 or below, 1N sodium hydroxide is added to bring the pH to about 7.30. Thus, the pH is maintained above 7.0. After 72 h incubation the desired ester hydrolysis reached about 70%, based on HPLC analysis. Enzyme reaction is filtered through a 0.2μ membrane to remove the insoluble material from the crude enzyme preparation. The clear enzyme reaction mix is extracted twice with ethyl acetate (1:1) at pH 7.0, which removes all the remaining esters, leaving only 5,6-dihydro-4H-pyrrolo(1,2-b)pyrazole-2-carboxylic acid in the aqueous phase. The aqueous phase containing the acid product is lyophilized and the recovered solid is dissolved in methanol. The salts that were not soluble in methanol are separated and discarded. Methanol containing 5,6-dihydro-4H-pyrrolo(1,2-b)pyrazole-2-carboxylic acid (pale yellow) is evaporated and about 0.5 g of 5,6-dihydro-4H-pyrrolo(1,2-b)pyrazole-2-carboxylic acid is recovered. The LC-MS and NMR data are consistent and indicated that only the desired acid is present with isomeric purity at 100%. The acid purity by HPLC is over 97%. HPLC conditions are: Prodigy ODS3 column 4.6×150 mm. Solvent A: 0.02% Trifluoroacetic acid (TFA) in water. Solvent B: 0.02% TFA in acetonitrile. Gradient used is, 90% A and 10% B at zero time with gradient reaching at 20 minutes, 5% A and 95% B and continue until 25 minutes.

Example 3

Nonselective Hydrolysis of Ester Isomers by Lipases

Under certain conditions such as excess amount of hydrolyzing enzyme and low substrate concentration, and prolonged incubation of the reaction would lead to hydrolysis of both ester isomers in a non-selective manner by the same lipases which otherwise would show very good selective hydrolysis of the desired ester isomer. Examples of such non-selective substrate hydrolysis conditions for the immobilized form of *C. antarctica* lipase B are: 23 g (10000 U/g) of the enzyme incubated with 2.5 g of the esters mix in 1 L of buffer at pH 7.25, 37° C. for 66 hours. For the immobilized enzyme preparation the activity units are defined as the ester synthesis unit as follows. One unit is the amount of enzyme that can synthesize 1μ mole of propyl laurate ester from propanol and lauric acid per minute. Similarly, for the soluble form of *C. antarctica* lipaseB, the conditions for non selective ester substrate hydrolysis are, 5 g enzyme (~1 20000 U/g) 2.5 g esters mix in 1L of phosphate buffer pH 7.25 at 37° C. for 18 h. The activity unit for soluble form of enzyme is defined as the amount of enzyme that can liberate the 1 μmol of butyric acid from tributyrin per minute at 25° C.

Under the above conditions the two preparations of *C. antarctica* lipase B shows non selective hydrolysis of both ester isomers 5,6-dihydro-4H-pyrrolo(1,2-b)pyrazole-2-carboxylic acid ethyl ester and 5,6-dihydro-4H-pyrrolo(1,2-b) pyrazole-3-carboxylic acid ethyl ester.

Example 4

Process Development with *Candida antarctica* LipaseB

Experiments with immobilized *C. antarctica* lipaseB and the esters mix 5,6-dihydro-4H-pyrrolo(1,2-b)pyrazole-2-carboxylic acid ethyl ester and 5,6-dihydro-4H-pyrrolo(1,2-b)pyrazole-3-carboxylic acid ethyl ester in buffer with pH 7.25 showed that this lipase can selectively hydrolyze the desired ester isomer. The typical enzyme hydrolysis reactions contain 6 g/L enzyme and the substrate esters mix could range from 10 to 133 g/L, under pH control using a pH stat and 3N ammonium hydroxide. If the pH is not controlled, the acid released from the enzyme reaction will lower the pH and if it reaches 5.0 or below, the enzyme activity could be inhibited and result in incomplete substrate hydrolysis leading to lower acid yield. In order to obtain complete hydrolysis of the desired ester isomer, the pH is maintained at about 7.0.

Example 5

Reaction of *C. antarctica* LipaseB with a Mixture 5,6-dihydro-4H-pyrrolo(1,2-b)pyrazole-2-carboxylic Acid Ethyl Ester and 5,6-dihydro-4H-pyrrolo(1,2-b)pyrazole-3-carboxylic Acid Ethyl Ester at 133 g/L To test the process conditions for large scale conversion, a mixture of ester substrates without further purification from their synthesis reactions is used. In a final volume of 30 ml 0.1M Tris-HCl buffer containing 10% acetonitrile, 4.05 g of a mixture 5,6-dihydro-4H-pyrrolo(1,2-b)pyrazole-2-carboxylic acid ethyl ester and 5,6-dihydro-4H-pyrrolo(1,2-b)pyrazole-3-carboxylic acid ethyl ester, and 0.2 g lipase Novozym 435 are incubated at 37° C. with pH control between 7.20-7.50. Ammonium hydroxide (3N) is used to control the pH using a pH-stat with an automatic control to add the alkali in order to maintain the pH. The reaction is set up in a jacketed glass vessel in a pH titrator (Brinkmann, model 718 Titrino). After the ammonium hydroxide consumption ceased, indicating that no more acid from ester hydrolysis is being formed, the reaction is stopped by solvent extraction. The reaction mix is extracted three times with equal volume (~30 ml) of ethyl acetate at about neutral pH until the aqueous phase is clear. Ethyl acetate extraction removed the remaining undesired ester along with other colored material from the reaction. The pH of the aqueous phase is lowered to ~3.0 with conc. HCl and the carboxylic acid product starts to precipitate. Additional HCl is added until the pH reached ~2.0, and stirring continued. The glass vessel is incubated at 4° C. for 1 h. The acid precipitate is filtered through a medium filter (Buchner funnel), and is air-dried. Specific examples using the above described conditions are shown in Table 2.

TABLE 2

Enzyme process conditions for ester hydrolysis and the yield of the acid product

| | Crude Ester Mix Prepn. Solvent | Crude substrate Conc (g/L) | Total Rxn Vol (0.1 M Tris-HCl pH 7.3) | Rxn Time (complete in 12 h) | Acid Recovered |
|---|---|---|---|---|---|
| 1 | DMF[1] | 4.04 g (133 g/L) | 30 mL | 19 h | 0.962 g |

TABLE 2-continued

Enzyme process conditions for ester hydrolysis and the yield of the acid product

| | Crude Ester Mix Prepn. Solvent | Crude substrate Conc (g/L) | Total Rxn Vol (0.1 M Tris-HCl pH 7.3) | Rxn Time (complete in 12 h) | Acid Recovered |
|---|---|---|---|---|---|
| 2 | DEE[2] | 4.05 g (133 g/L) | 30 mL | 17 h | 1.33 g |

[1]N,N-dimethylformamide (DMF)
[2]1,2-diethoxyethane (DEE)

The chemical analysis showed that the acid (entry 2 in Table 1) is 99.8% pure (HPLC method), contained 11% moisture, and 0.387% ash. The proton NMR, LC-MS and IR data confirmed the material obtained is the desired acid expected from the enzyme reaction.

What is claimed:

1. A process for the preparation of a bicyclic-heteroaryl-2-carboxylic acid 7 of the formula

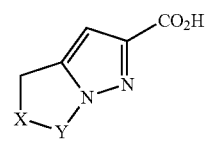

7 wherein Y is $(CH_2)_n$; n is 1; X is —$CH_2$—; which comprises enzymatic hydrolysis with an effective hydrolyzing enzyme selected from *C. antarctica* lipase B, *Aspergillus* sp. acylase, *Aspergillus oryzae* protease M, *C. rugosa* lipase, and lipase from *Pseudomonas* sp. of bicyclic-heteroaryl-2-carboxylic acid ester 6

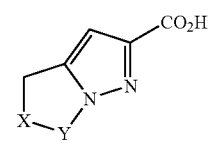

7 wherein X and Y are defined as above and $R_1$ is alkyl of 1 to 6 carbon atoms to produce the bicyclic-heteroaryl-2-carboxylic acid 7 of the formula

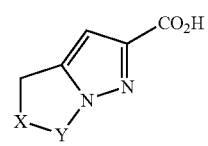

7 wherein X and Y are as defined as above and isolating the bicyclic-heteroaryl-2-carboxylic acid 7.

2. A process for the preparation of a bicyclic heteroaryl-2-carboxylic acid 7

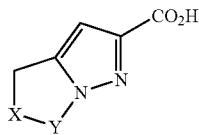

wherein Y is $(CH_2)_n$; n is 1; X is —$CH_2$—; which comprises enzymatic hydrolysis with an effective hydrolyzing enzyme selected from *C. antarctica* lipase B, *Aspergillus* sp. acylase, *Aspergillus oryzae* protease M, *C. rugosa* lipase, and lipase from *Pseudomonas* sp. of bicyclic heteroaryl-2-carboxylate 6 in a mixture of bicyclic heteroaryl-2-carboxylate 6 and bicyclic heteroaryl-3-carboxylate 5 where $R_1$ is alkyl of 1 to 6 carbon atoms of the formulae

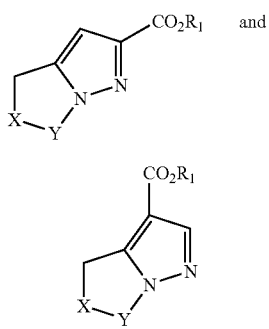

wherein Y is $(CH_2)_n$; n is 1; X is —$CH_2$—; to selectively produce a bicyclic heteroaryl-2-carboxylic acid 7 of the formula

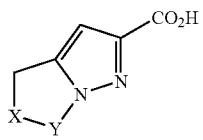

wherein X and Y are defined as above which comprises the steps of:

a) contacting a mixture of bicyclic heteroaryl-2-carboxylate 6 and bicyclic heteroaryl-3-carboxylate 5 wherein X, Y, and $R_1$ are as defined as above with an effective amount of an effective hydrolyzing enzyme selected from *C. antarctica* lipase B, *Aspergillus* sp. acylase, *Aspergillus oryzae* protease M, *C. rugosa* lipase, and lipase from *Pseudomonas* sp. in aqueous solvent at an effective pH range, for an effective time, optionally in a buffer, and optionally in the presence of a cosolvent;

b) maintaining the pH at about 6.5 to about 7.8 by the addition of a base;

c) removing the bicyclic heteroaryl-3-carboxylate 5 by organic solvent extraction;

d) separating the aqueous solvent and optionally adjusting the pH from about 2.0 to about 3.0;

e) isolating the bicyclic heteroaryl-2-carboxylic acid 7 of the formula

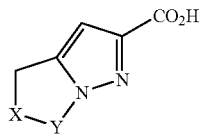

wherein X and Y are defined as above, as the carboxylic acid or as a pharmaceutically acceptable salt thereof.

3. The process according to claim 2 wherein the effective amount of the effective hydrolyzing enzyme is in the range of about 3 mg to 10 mg/ml.

4. The process according to claim 3 wherein the effective amount of the effective hydrolyzing enzyme is about 6 mg/ml.

5. The process of claim 2 further comprising an effective temperature of about 20 to 65° C.

6. The process according to claim 5 wherein the effective temperature is about 37° C.

7. The process according to claim 2 wherein the effective pH range is about 4.0 to about 10.0.

8. The process of claim 7 wherein the effective pH of the reaction is maintained at about 6.5 to 7.8 by the addition of a base.

9. The process according to claim 8 wherein the effective pH of the reaction is maintained at about 7.0 by the addition of a base.

10. The process according to claim 2 wherein the optional buffer is selected from phosphate salts or Tris-HCl buffer.

11. The process according to claim 10 wherein the buffer is Tris-HCl.

12. The process according to claim 2 wherein the optional cosolvent is selected from acetonitrile or N,N-dimethylformamide.

13. The process according to claim 12 wherein the cosolvent is acetonitrile.

14. The process according to claim 13 wherein the cosolvent acetonitrile is present in about 10% concentration.

15. The process according to claim 9 wherein the base is selected from sodium hydroxide or ammonium hydroxide.

16. The process according to claim 2 wherein the pH is adjusted to about 2.0 to about 3.0 with hydrochloric acid.

17. The process according to claim 2 wherein the effective time is about 9 to 72 hours.

18. A process for the preparation of bicyclic-heteroaryl-2-carboxylic acid having the formula 7

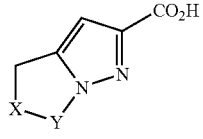

wherein Y is $(CH_2)_n$; n is 1; X is —$CH_2$—; which comprises enzymatic hydrolysis with an effective hydrolyzing enzyme selected from *C. antarctica* lipase B, *Aspergillus* sp. acylase, *Aspergillus oryzae* protease M, *C. rugosa* lipase, and lipase from *Pseudomonas* sp. of bicyclic-heteroaryl-2-carboxylic acid ester 6 wherein X, Y and R are defined as above and $R_1$ is alkyl of 1 to 6 carbon atoms or selectively in a mixture of bicyclic-heteroaryl-2-carboxylic acid ester 6 and bicyclicheteroaryl-3-carboxylic acid ester 5 wherein X, Y, and $R_1$ are defined as above of the formulae:
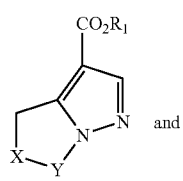
and
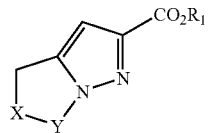
to produce a bicyclic-heteroaryl-2-carboxylic acid of the formula 7
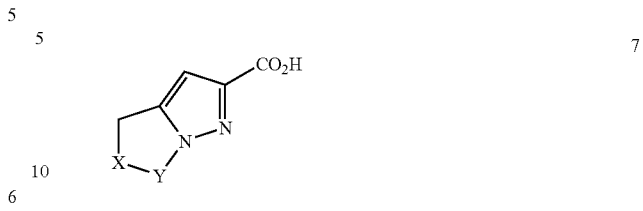
wherein X and Y are defined as above.
* * * * *